US008900299B2

United States Patent
Terwee

(10) Patent No.: US 8,900,299 B2
(45) Date of Patent: *Dec. 2, 2014

(54) METHOD IN EYE SURGERY

(75) Inventor: Thomas Terwee, Roden (NL)

(73) Assignee: AMO Groningen B.V., Groningen (NL)

(*) Notice: Subject to any disclaimer, the term of this patent is extended or adjusted under 35 U.S.C. 154(b) by 1008 days.

This patent is subject to a terminal disclaimer.

(21) Appl. No.: 12/551,528

(22) Filed: Aug. 31, 2009

(65) Prior Publication Data

US 2009/0319039 A1    Dec. 24, 2009

Related U.S. Application Data

(63) Continuation of application No. 11/538,911, filed on Oct. 5, 2006, now Pat. No. 7,582,113, which is a continuation of application No. 10/438,685, filed on May 15, 2003, now Pat. No. 7,160,324.

(60) Provisional application No. 60/381,262, filed on May 17, 2002.

(51) Int. Cl.
*A61F 2/16* (2006.01)
*A61F 9/00* (2006.01)

(52) U.S. Cl.
CPC ............ *A61F 9/0017* (2013.01); *Y10S 623/905* (2013.01); *Y10S 623/907* (2013.01)
USPC .......... 623/6.39; 623/6.37; 623/4.1; 623/905; 623/907

(58) Field of Classification Search
USPC ............ 623/4.1, 6.13, 6.16, 6.32, 6.34, 6.37, 623/6.39, 6.59, 6.61
See application file for complete search history.

(56) References Cited

U.S. PATENT DOCUMENTS

| | | | | |
|---|---|---|---|---|
| 4,373,218 A | * | 2/1983 | Schachar | 623/6.13 |
| 4,693,717 A | | 9/1987 | Michelson | |
| 4,919,151 A | | 4/1990 | Grubbs et al. | |
| 5,002,571 A | | 3/1991 | O'Donnell, Jr. et al. | |
| 5,266,074 A | * | 11/1993 | Nishi et al. | 623/6.39 |

(Continued)

FOREIGN PATENT DOCUMENTS

| | | |
|---|---|---|
| WO | WO 0022459 | 4/2000 |
| WO | WO 0022460 | 4/2000 |

(Continued)

OTHER PUBLICATIONS

Nishi et al. "Inhibition of Migrating Lens Epithelial Cells at the Capsular Bend Created by the Rectangular Optic Edge of a Posterior Chamber Intraocular Lens", Ophthalmic Surg Lasers 29:587-594 (1998).

(Continued)

*Primary Examiner* — Thomas J Sweet
*Assistant Examiner* — Cheryl Miller
(74) *Attorney, Agent, or Firm* — AMO Groningen B.V.

(57) ABSTRACT

A method for prevention of migration of epithelial cells in a capsular bag of an eye of a mammal is provided. The method comprises removing the natural lens of the eye from the capsular bag; introducing an object with at least one sharp edge into the capsular bag, in such a way that said sharp edge contacts the inside of the capsular bag to form a barrier preventing migration of epithelial cells across said barrier; and injecting a lens-forming composition into the capsular bag.

20 Claims, 1 Drawing Sheet

(56) References Cited

U.S. PATENT DOCUMENTS

| | | | |
|---|---|---|---|
| 5,628,795 A | 5/1997 | Langerman | |
| 6,186,148 B1* | 2/2001 | Okada | 128/898 |
| 6,228,115 B1 | 5/2001 | Hoffmann et al. | |
| 6,319,282 B1 | 11/2001 | Nishi | |
| 6,361,561 B1 | 3/2002 | Huo et al. | |
| 6,406,494 B1 | 6/2002 | Laguette et al. | |
| 6,468,306 B1 | 10/2002 | Paul et al. | |
| 6,533,769 B2* | 3/2003 | Holmen | 604/521 |
| 6,558,419 B1 | 5/2003 | Pham et al. | |
| 6,702,853 B1* | 3/2004 | Peyman | 623/6.39 |
| 7,060,095 B2* | 6/2006 | Ho et al. | 623/4.1 |
| 7,160,324 B2 | 1/2007 | Terwee | |
| 8,048,155 B2* | 11/2011 | Shadduck | 623/6.37 |
| 2002/0055776 A1* | 5/2002 | Juan et al. | 623/6.12 |
| 2003/0004569 A1* | 1/2003 | Haefliger | 623/6.34 |
| 2003/0028248 A1* | 2/2003 | Shahinpoor et al. | 623/4.1 |
| 2003/0105522 A1* | 6/2003 | Glazier | 623/6.13 |
| 2003/0208265 A1 | 11/2003 | Ho et al. | |

FOREIGN PATENT DOCUMENTS

| | | |
|---|---|---|
| WO | WO 0078251 | 12/2000 |
| WO | WO 0156508 A1 | 8/2001 |
| WO | WO 0176651 | 10/2001 |

OTHER PUBLICATIONS

Nishi et al. "Preventing posterior capsule opacification by creating a discontinuous sharp bend in the capsule", J Cataract Refract Surg 25:521-526 (1999).

Nishi et al. "Preventing lens epithelial cell migration using intraocular lenses with sharp rectangular edges", J Cataract Refract Surg 26:1543-1549 (2000).

* cited by examiner

METHOD IN EYE SURGERY

RELATED APPLICATIONS

This application is a continuation of application of patent application Ser. No. 11/538,911, filed Oct. 5, 2006, now U.S. Pat. No. 7,582,113, which is a continuation of application of patent application Ser. No. 10/438,685, filed May 15, 2003, now U.S. Pat. No. 7,160,324, which claims priority under 35 U.S.C. 119 to U.S. application Ser. No. 60/381,262, filed May 17, 2002, the entire contents of each of which applications are hereby incorporated by reference in their entirety for all purposes as if fully set forth herein.

FIELD OF THE INVENTION

The present invention relates to a method in connection with eye surgery, especially in connection with replacement of the natural lens of the eye with an artificial lens. More particularly, the present invention relates to preventing migration of epithelial cells within the lens capsule of the eye in connection with such lens replacement surgery.

BACKGROUND

The eye of a mammal is composed of a cornea, or clear outer tissue, which refracts light rays en route to the pupil, an iris which controls the size of the pupil, thus regulating the amount of light entering the eye, and a lens which focuses the incoming light through the vitreous fluid to the retina. The lens is embedded in a capsular bag. In the perfect eye, the light path from the cornea, through the lens and vitreous fluid to the retina is unobstructed. Any obstruction or loss in clarity within these structures causes scattering or absorption of light rays, resulting in diminished visual acuity. For example, the lens is susceptible to oxidative damage, trauma and infection.

As the body ages, the effects of oxidative damage accumulate, resulting in loss of lens flexibility and in denatured proteins that slowly coagulate, reducing lens transparency. The natural flexibility of the lens is essential for focusing light onto the retina by the process of accommodation. Accommodation allows the eye to adjust the field of vision for objects at different distances.

Lenticular cataract is a lens disorder resulting from the further progression of protein coagulation and calcification. There are four common types of cataracts: senile cataracts associated with aging and oxidative stress, traumatic cataracts which develop after a foreign body enters the lens capsule or following intense exposure to ionising radiation or infrared rays, complicated cataracts which are secondary to diseases such as diabetes mellitus or eye disorders such as detached retinas, glaucoma and retinitis pigmentosa, and toxic cataracts resulting from medical or chemical toxicity. Regardless of the cause, the disease results in impaired vision and may lead to blindness.

Treatment of such severe lens diseases requires surgical removal of the lens from the capsular bag. The surgical procedure typically involves phacoemulsification, followed by irrigation and aspiration. Implantation of an intraocular lens (IOL) following the extraction of a cataract is now a standard ophthalmic procedure. Current IOL:s include rigid, non-deformable lenses as well as rollable or foldable lenses. Furthermore, techniques wherein a low viscosity lens material is directly injected into the empty capsular bag and cured in situ as part of the surgical procedure to form an IOL, reducing surgical incisions to about 1 mm, have been suggested. In such a process the capsular bag is used as a mould to form the shape of the lens and thereby contribute to control its refraction.

In connection with the procedures described above for replacement of the natural lens with an implant, there may arise complications. Some of these complications are characterized by a migration of epithelial cells within the capsule, which form a cell layer occluding the lens.

Prevention of cell migration has been addressed by different investigators. Thus, it has been discovered that implantation of an IOL having sharp edges into rabbit eye lens capsules, such that the edges of the lens contact the inside of the capsular bag, leads to inhibition of migrating lens epithelial cells (Nishi et al, Ophthalmic Surg Lasers 29:587-594 (1998); Nishi and Nishi, J Cataract Refract Surg 25:521-526 (1999); Nishi et al, J Cataract Refract Surg 26:1543-1549 (2000)). The problem of epithelial cell migration is also addressed in U.S. Pat. No. 6,319,282, in the context of using capsular equator rings for maintenance or establishment of an extended capsular diaphragm. U.S. Pat. No. 6,319,282 describes a capsular equator ring having sharp edges for the inhibition of migration of subcapsular epithelium cells. None of the above documents mention the problem of prevention of epithelial cell migration in connection with injection of lens-forming materials into the capsule. The injection of a lens-forming material into the capsule, which material subsequently forms, through curing thereof in situ or otherwise, an intraocular lens, poses additional problems as regards the migration of epithelial cells. This is so because of the fact that the lens formed will completely fill the lens capsule, and in particular will not be removable in the manner of previously used flexible or non-flexible IOL:s. Thus, the problems posed by epithelial cell migration are more severe and difficult to address in the context of injected, lens forming materials than in the situations described by previous workers in the field.

SUMMARY OF THE INVENTION

It is therefore an object of the present invention to solve the above problems through providing a method which offers a combination of the recently proposed techniques for injecting a material, which forms a lens in situ after injection, with an approach to prevent epithelial cell growth during and after said injection.

Another object of the invention is to offer prevention of epithelial cell migration in connection with lens-forming material injection into the lens capsule, which is amenable to use with any of a variety of different devices.

Still another object of the invention is to make possible the treatment or prophylaxis of complications including secondary cataract formation, posterior capsule opacification, anterior capsule opacification, irregular growth and/or migration of epithelial cells etc, in the context of injection of a lens-forming material.

These objects, as well as others evident to the skilled person in light of the present disclosure, are met by the invention as claimed. Thus, a method for prevention of migration of epithelial cells in a capsular bag of an eye of a mammal is provided, which method comprises:

removing the natural lens of the eye from the capsular bag;
introducing an object with at least one sharp edge into the capsular bag, in such a way that said sharp edge contacts the inside of the capsular bag to form a barrier preventing migration of epithelial cells across said barrier; and
injecting a lens-forming composition into the capsular bag.

The steps of the method of the invention need not be performed in any particular order. However, for practical reasons, the step of removing the natural lens of the eye suitably precedes the steps of introducing a sharp-edged object and injecting a lens-forming composition. The latter two steps may then be performed in any order.

The invention is thus based on the realization that the establishment of a sharp edge against the capsular wall causes a sharp bend in the capsular wall and a barrier which effectively hinders the spread and growth of epithelial cells, and, inventively, that this fact may be exploited in the context of injection of a lens-forming composition into the eye.

BRIEF DESCRIPTION OF THE DRAWING

The invention may be further understood in view of the drawing in which.

DESCRIPTION OF PREFERRED EMBODIMENTS

The method of the invention is concerned with the prevention of epithelial cell migration. Such migration may appear as a complication following eye surgery to remove the natural lens of the eye, and may give rise to clouding of vision and other undesirable effects. Conditions characterized by migration of epithelial cells in the capsule of the eye, which may be addressed prophylactically or therapeutically by the method of the present invention, include secondary cataracts, posterior capsule opacification (PCO), anterior capsule opacification (ACO) and irregular growth or migration of epithelial cells causing capsular shrinkage.

The method of the present invention comprises removing the natural lens of the eye. This may be performed according to established practice within the art, for example by using a conventional surgical method involving an ultrasound probe, such as a phacoemulsification method involving aspiration. In order to facilitate the removal of the lens matrix, introduction of an object and the refilling with lens-forming liquid material, a capsulotomy, e g a capsulorhexis, is suitably prepared in the anterior wall of the capsular bag.

Further, the method of the present invention comprises introducing an object with at least one sharp edge into the capsular bag, in such a way that said sharp edge contacts the inside of the capsular bag. The contact of the sharp edge against the capsular bag forms a barrier to migration of epithelial cells. It is preferred that this barrier is established along the equator of the inside of the capsular bag, so that the introduced object for example contacts at least 50% of the capsular bag wall along the equator. For optimal results, it is preferred that as large a part as possible of the capsular bag wall along the equator is provided with the cell migration barrier. Thus, at least 75% is more preferred, and at least 95% even more preferred. In the ideal case, the introduced object establishes a sharp edge functioning as cell migration barrier along the whole of the capsular bag wall equator.

To fulfill this requirement, the introduced object may advantageously be an object suited for implantation into the capsule of the eye. Suitably, the object has roughly the shape of a filled or hollow cylinder, the radius of which is substantially larger than its height. The radius is furthermore large enough that the object, when introduced into the capsule, will "push against" the inside of the capsular wall, for example along the equator. In this way, the sharp edge of the object is brought to bear against the inside of the capsular bag, and the barrier to epithelial cell migration is formed.

Figure 1:
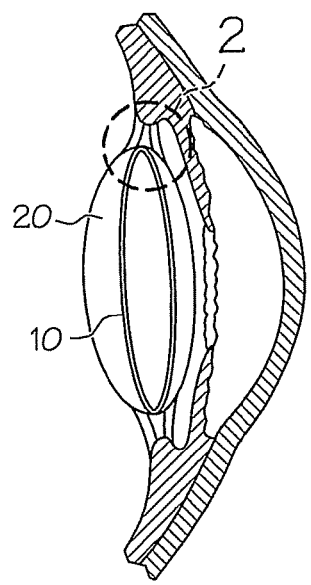
FIG. 1 provides a schematic view of an object introduced into the capsular bag in accordance with one embodiment of the invention.
Figure 2:
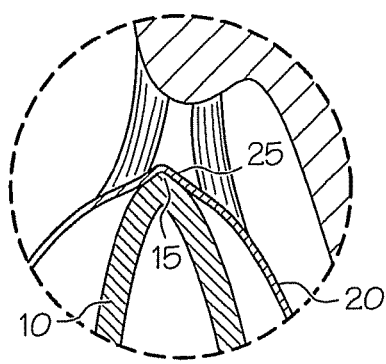
FIG. 2 provides an enlarged cross-sectional view of the portion A set forth in FIG. 1.

For example, FIG. 1 shows a schematic view of an eye of a mammal wherein the object 10 introduced into the capsular bag 20 is in the form of a ring which pushes against the inside of the capsular bag along the equator. A portion A of the object 10 in the capsular bag is shown in an enlarged, cross-sectional view in FIG. 2 to illustrate an example of one embodiment of the sharp edge 15 as it contacts the inside of the capsular bag at area 25.

The object introduced into the capsule establishes a sharp edge against the capsular wall. The term "sharp edge" as used herein denotes an edge with a radius that is preferably smaller than 2 micrometers (µm). The sharp edge is needed for that part of the device that is in contact with the capsular tissue, and it must point to the direction from where the migrating cells come. The device with the sharp edge is also preferably pressed with enough pressure to that capsular tissue to prevent the migrating cells to "lift" the device and grow under it. The pressure may be applied in different ways, such as by the internal pressure of the injected lens-forming composition or by mechanical connection to another, more or less opposite, part of the capsular bag. An example of this would be a sharp-edged ring on the posterior capsular side, which is attached via rather stiff connectors to a ring on the anterior side. After filling with lens material, the capsular bag will be put under tension and thus exercise pressure on both rings. In this case, the ring material must be such that it prevents cell migration over the side that is not in touch with the capsular tissue. An extra sharp edge on this, interior, side of the ring, to prevent cell migration over this edge is also preferred.

Among objects that are suitable for introduction into the capsule in the context of the method of the present invention, mention is made of capsular equatorial rings, intraocular lenses and haptics for intraocular lenses, all of which should fulfill the requirement of being provided with at least one sharp edge along their outer circumference. A capsular equatorial ring with sharp edges useful in the method of the invention is described in U.S. Pat. No. 6,319,282, hereby incorporated by reference. An intraocular lens with sharp edges useful in the method of the invention may be any IOL of conventional materials or other materials, which present at least one sharp edge along the circumference of the lens. The acrylic IOL AcrySof® MA6 0BM, the standard PMMA IOL and the silicon IOL CeeOn® Edge that were used in the experiments of Nishi and Nishi (J Cataract Refract Surg 25, 25:521-526 (1999); J Cataract Refract Surg 26:1543-1549 (2000)) are examples of suitable intraocular lenses having the requisite sharp edges. As an alternative, the object introduced for the purpose of establishing a barrier against cell migration may be a haptic of an intraocular lens, which haptic is provided with at least one sharp edge. In this case, the IOL connected to the haptic does not in itself need to be in close contact with the capsular wall. Rather, the haptic or, in most cases of commercially available IOL:s, haptics play the role of pushing against the inside of the capsule. The primary function of the haptic or haptics of keeping the IOL in place, is complemented by the added benefit of having a sharp edge that forms a barrier to cell migration.

Within the ambit of the method of the invention, the introduction of an object as described above in the capsular bag serves the function of providing the sharp edge against the capsular bag wall, whereas the problem of restoring the refractive power of the eye is solved by the injection of a lens-forming material into the capsule. In the case where the object providing the sharp edge in itself has optical properties, such as when an IOL is used, these may be used in combination with the optical properties of the injected lens-forming material. It is the aim of an injectable accommodating lens to restore accommodation, which would otherwise be lost after cataract surgery due to implanting of a monofocal IOL or simply due to aging of the eye (presbyopia). Normally, monofocal IOL patients and presbyopic humans need spectacles in order to have good vision over all distances, from nearby (reading distance) to infinity. The advantage of also having an artificial accommodating lens, made from an injected lens-forming composition, is ideally to enable the patient to become independent of spectacles. That means that the base refraction of the new lens must be such that, in combination with the accommodating range of the new lens, the patient is able to see a focused image from near to infinity, without the help of spectacles. The base refraction is influenced by many factors, e g the length of the eye, the optical power of the cornea, the internal dimensions of the eye and the refractive power of the refilled lens. This refractive power of the refilled lens may in turn be influenced by a number of factors, e g the shape of the capsular bag, the refractive index of the injectible lens material, the degree of filling of the capsular bag. Through implanting of a sharp-edged lens inside the capsular bag in combination with the lens-forming injectible material, the refractive power can be influenced further. The procedure gives more degrees of freedom to control the refractive power of the lens. Such a lens only has an effect on the refractive power when its refractive index differs from the refractive index of the lens-forming material.

As noted above, the method according to the present invention further comprises injecting into the capsular bag of a lens-forming composition. The composition consists of a partially polymerized material, which can undergo a curing process in the eye and thereby form a solid lens implant. The lens implant acts as a substitute for the natural lens and aims to restore the features of the natural lens of a young eye.

Materials suitable for injection and subsequent formation of an IOL have been disclosed, for example in WO00/22459, WO00/22460 and WO01/76651. Briefly, a suitable lens-forming composition may be a curable composition. The composition may further comprise polysiloxane. A preferred polysiloxane composition for use in the method of the invention has a specific gravity of greater than about 1.0, a refractive index suitable for restoring the refractive power of the natural crystalline lens, and a viscosity suitable for injection of the composition through a standard cannula. These properties can be attained for example with a composition comprising a siloxane monomer —$R_aR_bSiO$—, wherein $R_a$ and $R_b$ are the same or different alkyl or phenyl groups, of which at least one is substituted with at least one fluorine atom. A further useful composition is one that comprises polysiloxane that is a terpolymer or a higher polymer of three or more different siloxane monomer units. A particularly suitable lens-forming composition comprises polysiloxane that is a terpolymer of (a) dimethylsiloxane, (b) methylphenylsiloxane or diphenylsiloxane, and (c) trifluoropropylmethylsiloxane monomers. Furthermore, the polysiloxanes forming part of such suitable lens-forming compositions may be provided with groups that are capable of being crosslinked, the composition then further comprising a crosslinking agent and, optionally, an effective amount of a catalyst.

Another type of material that has been proposed as suitable for injection to form an IOL, and is therefore contemplated within the context of the present invention, is a hydrogel formulation.

As an exemplary embodiment of the method according to the present invention, the following steps are performed: First, the natural lens of the eye is removed by phacoemulsification involving preparing a capsulorhexis. Second, an capsular equatorial ring with sharp edges is inserted into the capsule through the capsulorhexis. Third, a lens-forming composition comprising a mixture of functional and non-functional poly(dimethyl-co-diphenylco-trifluoropropylmethyl)siloxanes is injected through the capsulorhexis using a syringe The method according to the invention is applicable in any mammal including man. Most situations in which the method will be applicable will probably concern attempts at restoring of eye-sight in a human patient.

The invention claimed is:

1. Method for forming a lens in situ in an eye of a mammal, comprising:
    removing the natural lens of the eye from the capsular bag;
    introducing an optic with a radius and at least one sharp edge into the capsular bag and positioning the optic within the capsular bag with the at least one sharp edge contacting an inside wall of the capsular bag;
    wherein the radius of the optic is large enough such that the optic will span a diameter of the capsular bag at approximately the equator so as to push the at least one sharp edge against the inside wall of the capsular bag at approximately the equator to create a barrier;
    injecting a lens-forming composition into the capsular bag to fill the capsular bag; and
    curing the lens-forming composition to form a lens having an outer circumference, wherein the formed lens completely fills the capsular bag and the at least one sharp edge remains in contact with an inside wall of the capsular bag after lens formation;
    wherein the optic has optical properties that may be used in combination with optical properties of the injected lens-forming composition.

2. Method according to claim 1, wherein the lens-forming composition comprises polysiloxane.

3. Method according to claim 2, wherein the lens-forming composition comprising polysiloxane has a specific gravity of greater than about 1.0, a refractive index suitable for restoring the refractive power of the natural crystalline lens, and a viscosity suitable for injection of the composition through a standard cannula.

4. Method according to claim 2, wherein the lens-forming composition comprises polysiloxane of a siloxane monomer unit —$R_aR_bSiO$—, wherein $R_a$ and $R_b$ are the same or different alkyl or phenyl groups, at least one of which is substituted with at least one fluorine atom.

5. Method according to claim 2, wherein the lens-forming composition comprises polysiloxane that is a terpolymer or higher polymer of three or more different siloxane monomer units.

6. Method according to claim 2, wherein the lens-forming composition comprises polysiloxane that is a terpolymer of (a) dimethylsiloxane, (b) methylphenylsiloxane or diphenylsiloxane, and (c) trifluoropropylmethylsiloxane monomers.

7. Method according to claim 2, wherein the lens-forming composition comprises polysiloxane having crosslinkable groups, and further comprises a crosslinking agent and optionally an effective amount of a catalyst.

8. Method according to claim 1, wherein the lens-forming composition comprises a hydrogel.

9. The method of claim 1, further comprising pressing the inside wall of the capsular bag with enough pressure to prevent migration of epithelial cells.

10. The method of claim 1, further comprising filling the capsular bag with the lens-forming composition and, after filling the capsular bag, putting the capsular bag under tension.

11. Method for forming a lens in situ in an eye of a mammal, comprising:

removing the natural lens of the eye from the capsular bag;
    introducing an optic with a radius and at least one sharp edge along an outer circumference of the optic into the capsular bag and positioning the optic within the capsular bag, with the at least one sharp edge contacting an inside wall of the capsular bag;
    wherein the radius of the optic is large enough such that the at least one sharp edge will push the inside wall of the capsular bag at approximately the equator to create a barrier;
    injecting a lens-forming composition into the capsular bag to fill the capsular bag; and
    curing the lens-forming composition to form a lens having an outer circumference, wherein the formed lens completely fills the capsular bag and the optic remains in the capsular bag, the at least one sharp edge remaining in contact with an inside wall of the capsular bag after lens formation by curing of the lens-forming composition;
    wherein the optic has optical properties that may be used in combination with optical properties of the injected lens-forming composition.

12. The method of claim 11, further comprising pressing the inside wall of the capsular bag with enough pressure to prevent migration of epithelial cells.

13. The method of claim 11, further comprising filling the capsular bag with the lens-forming composition and, after filling the capsular bag, putting the capsular bag under tension.

14. Method according to claim 11, wherein the lens-forming composition comprises polysiloxane.

15. Method according to claim 14, wherein the lens-forming composition comprising polysiloxane has a specific gravity of greater than about 1.0, a refractive index suitable for restoring the refractive power of the natural crystalline lens, and a viscosity suitable for injection of the composition through a standard cannula.

16. Method according to claim 14, wherein the lens-forming composition comprises polysiloxane of a siloxane monomer unit —$R_aR_bSiO$—, wherein $R_a$ and $R_b$ are the same or different alkyl or phenyl groups, at least one of which is substituted with at least one fluorine atom.

17. Method according to claim 14, wherein the lens-forming composition comprises polysiloxane that is a terpolymer or higher polymer of three or more different siloxane monomer units.

18. Method according to claim 14, wherein the lens-forming composition comprises polysiloxane that is a terpolymer of (a) dimethylsiloxane, (b) methylphenylsiloxane or diphenylsiloxane, and (c) trifluoropropylmethylsiloxane monomers.

19. Method according to claim 14, wherein the lens-forming composition comprises polysiloxane having crosslinkable groups, and further comprises a crosslinking agent and optionally an effective amount of a catalyst.

20. Method according to claim 11, wherein the lens-forming composition comprises a hydrogel.

\* \* \* \* \*